United States Patent [19]
Mitchell et al.

[11] Patent Number: 6,087,448
[45] Date of Patent: Jul. 11, 2000

[54] SOLID SUPERABSORBENT MATERIAL CONTAINING A POLY(VINYLGUANIDINE) AND AN ACIDIC WATER-ABSORBING RESIN

[75] Inventors: Michael A. Mitchell, Lake Zurich; Thomas W. Beihoffer, Arlington Heights, both of Ill.

[73] Assignee: AMCOL International Corporation, Arlington Heights, Ill.

[21] Appl. No.: 08/974,126

[22] Filed: Nov. 19, 1997

[51] Int. Cl.$^7$ ............................ C08L 33/02; C08L 39/00
[52] U.S. Cl. ........................ 525/217; 525/207; 525/209
[58] Field of Search .................... 525/207, 217, 525/212, 209, 210, 57, 54.3

[56] References Cited

U.S. PATENT DOCUMENTS

| | | | |
|---|---|---|---|
| 3,790,537 | 2/1974 | Panzer et al. | |
| 3,856,715 | 12/1974 | Corte et al. | |
| 3,878,170 | 4/1975 | Panzer et al. | |
| 4,004,074 | 1/1977 | Gerecht et al. | 526/305 |
| 4,018,826 | 4/1977 | Gless, Jr. et al. | |
| 4,818,598 | 4/1989 | Wong | 428/284 |
| 5,085,787 | 2/1992 | Pinschmidt, Jr. et al. | 252/8.551 |
| 5,260,385 | 11/1993 | Iio | 525/328.2 |
| 5,274,018 | 12/1993 | Tanaka et al. | 524/166 |
| 5,665,843 | 9/1997 | Iio | 526/310 |
| 5,669,894 | 9/1997 | Goldman et al. | 604/368 |

FOREIGN PATENT DOCUMENTS

| | | | |
|---|---|---|---|
| WO 96/15163 | 5/1996 | WIPO | C08F 20/56 |
| WO 96/15180 | 5/1996 | WIPO | C08J 5/02 |
| WO 96/17681 | 6/1996 | WIPO | B01J 20/00 |
| WO 98/24832 | 6/1998 | WIPO | C08J 3/075 |
| WO 98/37149 | 8/1998 | WIPO | C08L 101/14 |

OTHER PUBLICATIONS

Hayashi et al., *Chemical Abstracts*, vol. 109, (1988), No. 10, p. 12.
Matei et al., *Omagiu Raluca Ripan*, pp. 363–374 (1966), abstract only.

*Primary Examiner*—Christopher Henderson
*Attorney, Agent, or Firm*—Marshall, O'Toole, Gerstein, Murray & Borun

[57] ABSTRACT

Poly(vinylguanidine)-based superabsorbent gels are disclosed. The superabsorbent gels either comprise a mixture of a poly(vinylguanidine) polymer and an acidic water-absorbing polymer, like polyacrylic acid, or comprise a salt of a poly(vinylguanidine) polymer.

7 Claims, No Drawings ously expanded further absorption is limited by the crosslinks in the polymer
SOLID SUPERABSORBENT MATERIAL CONTAINING A POLY(VINYLGUANIDINE) AND AN ACIDIC WATER-ABSORBING RESIN

FIELD OF THE INVENTION

The present invention relates to superabsorbent gels containing a poly(vinylguanidine), or a salt thereof. The superabsorbent gels comprise a poly(vinylguanidine), and preferably a poly(vinylguanidine) admixed with an acidic superabsorbent polymer, like a polyacrylic acid, or comprise a salt of a poly(vinylguanidine).

BACKGROUND OF THE INVENTION

Water-absorbing resins are widely used in sanitary goods, hygienic goods, wiping cloths, water-retaining agents, dehydrating agents, sludge coagulants, disposable towels and bath mats, disposable door mats, thickening agents, disposable litter mats for pets, condensation-preventing agents, and release control agents for various chemicals. Water-absorbing resins are available in a variety of chemical forms, including substituted and unsubstituted natural and synthetic polymers, such as hydrolysis products of starch acrylonitrile graft polymers, carboxymethylcellulose, crosslinked polyacrylates, sulfonated polystyrenes, hydrolyzed polyacrylamides, polyvinyl alcohols, polyethylene oxides, polyvinylpyrrolidines, and polyacrylonitriles.

Such water-absorbing resins are termed "superabsorbent polymers," or SAPs, and typically are lightly crosslinked hydrophilic polymers. SAPs are generally discussed in Goldman et al. U.S. Pat. No. 5,669,894. SAPs can differ in their chemical identity, but all SAPs are capable of absorbing and retaining amounts of aqueous fluids equivalent to many times their own weight, even under moderate pressure. For example, SAPs can absorb one hundred times their own weight, or more, of distilled water. The ability to absorb aqueous fluids under a confining pressure is an important requirement for an SAP in a hygienic article, like a diaper.

The dramatic swelling and absorbent properties of SAPs are attributed to (a) electrostatic repulsion between the charges along the polymer chains, and (b) osmotic pressure of the counter ions. It is known, however, that these absorption properties are drastically reduced in solutions containing electrolytes, such as saline, urine, and blood. The polymers do not function as effective SAPs in the presence of such physiologic fluids.

The decreased absorbency of electrolyte-containing liquids is illustrated by the absorption properties of a typical, commercially available SAP, i.e., sodium polyacrylate, in deionized water and in 0.9% by weight sodium chloride (NaCl) solution. The sodium polyacrylate can absorb 146.2 grams (g) of deionized water per gram of SAP (g/g) at 0 psi, 103.8 g of deionized water per gram of polymer at 0.28 psi, and 34.3 g of deionized water per gram of polymer of 0.7 psi. In contrast, the same sodium polyacrylate is capable of absorbing only 43.5 g, 29.7 g, and 24.8 g of 0.9% aqueous NaCl at 0 psi, 0.28 psi, and 0.7 psi, respectively. The absorption capacity of SAPs for body fluids, like urine or menses, therefore, is dramatically lower than for deionized water because such fluids contain electrolytes. This dramatic decrease in absorption is termed "salt poisoning."

The salt poisoning effect has been explained as follows. Water-absorption and water-retention characteristics of SAPs are attributed to the presence of ionizable functional groups in the polymer structure. The ionizable groups typically are carboxyl groups, a high proportion of which are in the salt form when the polymer is dry, and which undergo dissociation and solvation upon contact with water. In the dissociated state, the polymer chain contains a plurality of functional groups having the same electric charge and, thus, repel one another. This electronic repulsion leads to expansion of the polymer structure, which, in turn, permits further absorption of water molecules. Polymer expansion, however, is limited by the crosslinks in the polymer structure, which are present in a sufficient number to prevent solubilization of the polymer.

It is theorized that the presence of a significant concentration of electrolytes interferes with dissociation of the ionizable functional groups, and leads to the "salt poisoning" effect. Dissolved ions, such as sodium and chloride ions, therefore, have two effects on SAP gels. The ions screen the polymer charges and the ions eliminate the osmotic imbalance due to the presence of counter ions inside and outside of the gel. The dissolved ions, therefore, effectively convert an ionic gel into a nonionic gel, and swelling properties are lost.

The most commonly used SAP for absorbing electrolyte-containing liquids, like urine, is neutralized polyacrylic acid, i.e., containing at least 50%, and up to 100%, neutralized carboxyl groups. Neutralized polyacrylic acid, however, is susceptible to salt poisoning. Therefore, to provide an SAP that is less susceptible to salt poisoning, either an SAP different from neutralized polyacrylic acid must be developed, or the neutralized polyacrylic acid must be modified or treated to at least partially overcome the salt poisoning effect.

Prior investigators have attempted to counteract the salt poisoning effect and thereby improve the performance of SAPs with respect to absorbing electrolyte-containing liquids, such as menses and urine. For example, Tanaka et al. U.S. Pat. No. 5,274,018 discloses an SAP composition comprising a swellable hydrophilic polymer, like polyacrylic acid, and an amount of an ionizable surfactant sufficient to form at least a monolayer of surfactant on the polymer. In another embodiment, a cationic gel, like a gel containing quaternized ammonium groups and in the hydroxide (i.e., OH) form, is used with an anionic gel (i.e., a polyacrylic acid) to remove electrolytes from the solution by ion exchange.

Wong U.S. Pat. No. 4,818,598 discloses admixing a fibrous anion exchange material, like DEAE cellulose, and a hydrogel, like a polyacrylate, to improve absorption properties. WO 96/17681 discloses admixing an anionic SAP, like polyacrylic acid, with a polysaccharide-based cationic SAP to overcome the salt poisoning effect. Similarly, WO 96/15163 discloses admixing a cationic SAP having at least 20% of the functional groups in a basic (i.e., OH) form with a cationic exchanges resin, i.e., a nonswelling ion exchange resin, having at least 50% of the functional groups in the acid form. WO 96/15180 discloses an absorbent material comprising an anionic SAP, e.g., a polyacrylic acid and an anion exchange resin, i.e., a nonswelling ion exchange resin.

These references disclose combinations that attempt to overcome the salt poisoning effect. It would be desirable, however, to provide an SAP that exhibits exceptional absorbency and retention, like a sodium polyacrylate, and, therefore, can be used alone as an SAP. It also would be desirable to admix such an SAP with polyacrylic acid, or another acid-containing SAP, to overcome the salt poisoning effect.

Resins based on guanidine are known to be strongly basic, and, therefore, found use in early strong base ion exchange resins. The guanidine-based resins were condensation polymers of formaldehyde and guanidine. The preparation of poly(vinylguanidine) for use in an ion exchange resin is disclosed in Corte et al. U.S. Pat. No. 3,856,715. The synthesis of poly(vinylguanidine) also is disclosed in I. Matie et al., *Omagin Raluca Ripan* (Romanian) pages 363–374 (1966). This invention, however, is directed to poly(vinylguanidines) that behave as an SAP, and help overcome the salt poisoning effect.

SUMMARY OF THE INVENTION

The present invention is directed to poly(vinylguanidine)-based superabsorbent gels. A poly(vinylguanidine) polymer (i.e., a poly(VG) polymer) can be used in conjunction with an acidic water-absorbing resin, like polyacrylic acid, to help overcome the salt poisoning effect, or a salt of a poly(vinylguanidine) polymer can be used alone as an SAP. The poly(vinylguanidine) polymer also can be used, alone, as an SAP to absorb and retain acidic media. More particularly, a poly(vinylguanidine) used as an SAP, or as a component of an SAP, is lightly crosslinked and, in preferred embodiments, is surface treated to improve absorption properties.

Accordingly, one aspect of the present invention is to provide an SAP having absorbency and retention properties comparable to a conventional SAP, like sodium polyacrylate. A present SAP is produced by neutralizing a poly(vinylguanidine) with a sufficient amount of acid, like hydrochloric acid, such that at least about 10%, i.e., about 10% to 100%, of the amine-functional groups are neutralized. The resulting poly(vinylguanidine) salt is an excellent SAP for absorbing aqueous media.

In accordance with another important aspect of the present invention, a lightly crosslinked poly(vinylguanidine), alone and unneutralized, can be used to absorb and retain acidic aqueous media. The acidic aqueous media converts the low-absorbing poly(vinylguanidine) to a highly absorbing poly(vinylguanidine) salt, i.e., converts the polymer to an SAP, during absorption. A poly(vinylguanidine), therefore, is an excellent resin for cleaning acid spills and the remediation of acidic species.

Yet another aspect of the present invention is to provide an improved SAP that overcomes the salt poisoning effect of electrolytes. In particular, the improved SAP material contains a mixture of an acidic swellable resin, like polyacrylic acid, and a poly(vinylguanidine).

These and other aspects and advantages of the present invention will become apparent from the following detailed description of the preferred embodiments.

DETAILED DESCRIPTION OF THE PREFERRED EMBODIMENTS

The present invention is directed to: (a) use of a poly(vinylguanidine), and salts thereof, as SAPs, and (b) an improved SAP material comprising an admixture of a poly(vinylguanidine) and an acidic water-absorbing resin.

Poly(vinylguanidines) are a relatively noninvestigated class of polymers. Principally, poly(vinylguanidines) have been suggested as ion exchange resins. A poly(vinylguanidine) has the general structural formula (I):

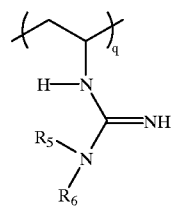

wherein q is a number from 10 to about 10,000, and $R_5$ and $R_6$, independently, are selected from the group consisting of hydrogen, $C_1$–$C_4$ alkyl, $C_3$–$C_6$ cycloalkyl, benzyl, phenyl, alkyl-substituted phenyl, naphthyl, and similar aliphatic and aromatic groups. The alkyl $R_5$ and $R_6$ groups can be branched or straight chained, and the $R_5$ and $R_6$ groups can be substituted or unsubstituted.

In general, an uncrosslinked poly(vinylguanidine) is a water-soluble polymer having many potential practical applications, such as in water treatment, personal care products, catalysts, fertilizers, explosives, and ion exchange resins. Poly(vinylguanidine) is rendered water insoluble by crosslinking the polymer. Polyvinylguanidines, and salts thereof, have not been considered for use as an SAP.

A poly(vinylguanidine) can be synthesized from a poly(vinylamine) polymer. Typically, a poly(vinylamine) polymer is produced by hydrolysis of poly(N-vinylformamide), under either acid or basic conditions. Poly(vinylamine) also can be produced from other poly(N-vinylamides), like poly(N-vinylacetamide), poly(N-vinylpropionamide), and poly(N-vinylsuccinamide). In the preparation of a poly(vinylguanidine), it is desirable that hydrolysis of the poly(vinylamide) is substantially to essentially complete, i.e., about 10% to 100% complete, and preferably about 30% to 100% complete. To achieve the full advantage of the present invention, at least about 50%, and more preferably at least about 90%, of the amide groups are hydrolyzed to an amine functionality. The amine-functional polymer can contain other copolymerizable units, i.e., other monoethylenically unsaturated monomers, as long as the polymer is substantially, i.e., at least 10%, and preferably at least 25%, vinylamine units. To achieve the full advantage of the present invention, the polymer contains at least 50%, and more preferably at least 75%, vinylamine units.

A poly(vinylguanidine) of the present invention preferably is prepared by reacting a polyvinylamine with a cyanamide having the formula $R_5R_6N$-CN. The cyanamide reacts with the amino groups of the poly(vinylamine) to provide a poly(vinylguanidine) of the present invention. The $R_5$ and $R_6$ groups can be, for example, hydrogen, $C_1$–$C_4$ alkyl, $C_3$–$C_6$ cycloalkyl, phenyl, benzyl, alkyl-substituted phenyl, naphthyl, and similar aliphatic and aromatic groups. The alkyl $R_5$ and $R_6$ groups can be straight or branched. The $R_5$ and $R_6$ groups can be substituted or unsubstituted. The poly(vinylamine) used in the synthesis of a poly(vinylguanidine) can be crosslinked or uncrosslinked, and can contain other monomer units in addition to vinylamine.

The present method, therefore, can be used to manufacture either crosslinked or uncrosslinked poly(vinylguanidine). The following example illustrates the manufacture of an uncrosslinked poly(vinylguanidine).

EXAMPLE 1

Preparation of Poly(vinylguanidine) (Poly(VG))

To 500 ml of an aqueous solution of poly(vinylamine) (1.98% solids, 93% hydrolyzed) was added 38.5 ml of 6M hydrochloric acid and 9.65 g of cyanamide ($H_2NCN$). The resulting solution was heated under reflux for 8 hours. The solution next was diluted to a volume of 3L (liters) with a 5% sodium hydroxide feed solution, then ultrafiltered ($M_W$ cut off of 100,000) with 15L of a 5% sodium hydroxide feed solution, followed by 15L of deionized water feed. The resulting product was concentrated to a 2.6% solids solution, having a pH 11.54. A poly(vinylamine) solution has a pH 10.0. The 2.6% solids solution gave a negative silver nitrate test, and a gravimetric analysis of the polymer, after the addition of HCl, gave the following composition: vinylguanidine 90%, vinylformamide 7%, and vinylamine 3%. Infrared analysis shows a strong absorption at 1651 $cm^{-1}$, which is not present in poly(vinylamine), and corresponds to a C=N stretch.

The present method of manufacturing a poly (vinylguanidine) can also be used in the manufacture of a crosslinked poly(vinylguanidine). As described above, SAPs are crosslinked to a sufficient extent such that the polymer is water insoluble. Crosslinking serves to render the poly (vinylguanidine) polymers substantially water insoluble, and, in part, serves to determine the absorptive capacity of the polymers. For use in absorption applications, the poly (vinylguanidine) is lightly crosslinked, i.e., has a crosslinking density of less than about 20%, preferably less than about 10%, and most preferably about 0.01% to about 7%.

When used, a crosslinking agent most preferably is included in an amount of less than about 7 wt %, and typically about 0.1 wt % to about 5 wt %, based on the total weight of monomers. A poly(vinyl-guanidine) can be crosslinked by two different pathways. One pathway utilizes olefinically unsaturated crosslinking monomers that copolymerize with the N-vinylamide, and, therefore, form a part of the polymeric backbone. The crosslinked poly(N-vinylamide) then is hydrolyzed to provide crosslinked poly (vinyl-amine), which in turn is converted into a crosslinked poly(vinylguanidine).

Examples of crosslinking polyvinyl monomers used in the preparation of a crosslinked poly(vinylamine) include, but are not limited to, polyacrylic (or polymethacrylic) acid esters represented by the following formula (II); and bisacrylamides, represented by the following formula (III).

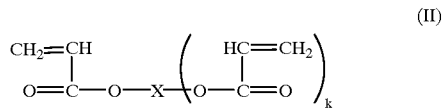

(II)

wherein x is ethylene, propylene, trimethylene, hexamethylene, 2-hydroxypropylene, —(CH$_2$CH$_2$O)$_n$CH$_2$CH$_2$—, or

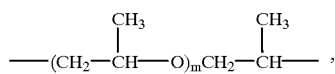

n and m are each an integer 5 to 40, and k is 1 or 2;

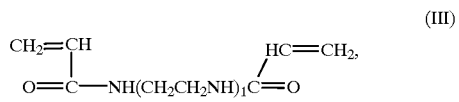

(III)

wherein l is 2 or 3.

The compounds of formula (II) are prepared by reacting polyols, such as ethylene glycol, propylene glycol, trimethylolpropane, 1,6-hexanediol, glycerin, pentaerythritol, polyethylene glycol, or polypropylene glycol, with acrylic acid or methacrylic acid. The compounds of formula (III) are obtained by reacting polyalkylene polyamines, such as diethylenetriamine and triethylenetetramine, with acrylic acid.

Specific crosslinking monomers include, but are not limited to, 1,4-butanediol diacrylate, 1,4-butanediol dimethacrylate, 1,3-butylene glycol diacrylate, 1,3-butylene glycol dimethacrylate, diethylene glycol diacrylate, diethylene glycol dimethacrylate, ethoxylated bisphenol A diacrylate, ethoxylated bisphenol A dimethacrylate, ethylene glycol dimethacrylate, 1,6-hexanediol diacrylate, 1,6-hexanediol dimethacrylate, neopentyl glycol dimethacrylate, polyethylene glycol diacrylate, polyethylene glycol dimethacrylate, triethylene glycol diacrylate, triethylene glycol dimethacrylate, tripropylene glycol diacrylate, tetraethylene glycol diacrylate, tetraethylene glycol dimethacrylate, dipentaerythritol pentaacrylate, pentaerythritol tetraacrylate, pentaerythritol triacylate, trimethylolpropane triacrylate, trimethylolpropane trimethacrylate, tris(2-hydroxyethyl)isocyanurate triacrylate, tris(2-hydroxyethyl)isocyanurate trimethacrylate, divinyl esters of a polycarboxylic acid, diallyl esters of a polycarboxylic acid, triallyl terephthalate, diallyl maleate, diallyl fumarate, hexamethylenebismaleimide, trivinyl trimellitate, divinyl adipate, diallyl succinate, a divinyl ether of ethylene glycol, cyclopentadiene diacrylate, or mixtures thereof. Compounds like divinylbenzene and divinyl ether also can be used to crosslink the poly(N-vinylamide). Especially preferred crosslinking agents are N,N'-methylenebisacrylamide, N,N'-methylenebismethacrylamide, ethylene glycol dimethacrylate, and trimethylolpropane triacrylate.

The following examples illustrate preparation of a crosslinked poly(vinylamine), which then can be used to prepare a poly(VG), as set forth in Example 1.

EXAMPLE 2

A monomer mixture containing N-vinylformamide (250 grams), deionized water (250 grams), methylenebisacrylamide (1.09 grams), and V-50 initiator (0.42 grams) was placed in a shallow dish, then polymerized under an ultraviolet lamp at 15 mW/cm$^2$ for 25 minutes such that the mixture polymerized into a rubbery gel. The concentrated poly(N-vinylformamide) then was treated with a sodium borohydride/sodium hydroxide solution to yield a lightly crosslinked poly(vinyl-amine). Sodium formate present in the crosslinked poly(vinylamine) can be removed by washing the resin with acetone/water mixtures.

Poly(vinylguanidine) also can be crosslinked in solution by suspending or dissolving uncrosslinked poly (vinylguanidine) in an aqueous medium, then adding a di- or polyfunctional compound capable of crosslinking the poly (vinylguanidine) by reaction with the guanidino groups of the polymer. The poly(vinylguanidine) can be in a free base form or can be in a salt form. Such crosslinking agents include, for example, monofunctional aldehydes (e.g., formaldehyde and acetaldehyde), multifunctional aldehydes (e.g., glutaraldehyde), multifunctional acrylates (e.g., butanediol diacrylate, TMPTA), halohydrins (e.g., epichlorohydrin), dihalides (e.g., dibromopropane), disulfonate esters (e.g., WS(O$_2$)O—(CH$_2$)$_n$—OS(O)$_2$W, wherein n is one to 10, and W is methyl or tosyl), multifunctional epoxies (e.g., ethylene glycol diglycidyl ether), melamine resins (e.g., CYMEL 301, CYMEL 303, CYMEL 370, and CYMEL 373 from Cytec Industries, Wayne, N.J.), hydroxymethyl ureas (e.g., N,N'-dihydroxymethyl-4,5-dihydroxyethyleneurea).

In general, the crosslinking agent should be water or alcohol soluble, and possess sufficient reactivity with a poly(vinylguanidine) such that crosslinking occurs in a controlled fashion, preferably at a temperature of about 25° C. to about 150° C. Preferred crosslinking agents are ethylene glycol diglycidyl ether (EGDGE), a water-soluble diglycidyl ether and dihaloalkanes, especially dibromoalkanes.

The following example illustrates light crosslinking of a poly(vinylguanidine) of the present invention using a polyfunctional crosslinking agent that reacts with the amino groups of the polymer.

EXAMPLE 3

Preparation of a Crosslinked Poly(VG) Resin

The 2.6% solids solution of Example 1 was further concentrated to 12.5% solids by distillation. To this 12.5% solids solution was added 1 mole % EGDGE, and the resulting solution was heated in a 60° C. oven for 5 hours to form a gel of lightly crosslinked poly(vinylguanidine). A portion of the gel was dried, granulated, rehydrated 70 mole % with 2N HCl and dried again. The dried, lightly crosslinked poly(vinylguanidine) then was ground to form a particulate material capable of absorbing water of acid solutions. The gel exhibited the following absorption characteristics with respect to 0.9% aqueous sodium chloride (NaCl):

$AUNL^{1)}$=31.2 g/g (1 hr.); 32.7 g/g (3 hr.)

$AUL^{2)}$(0.28 psi)=21 g/g (1 hr.); 22.4 g/g (3 hr.)

$AUL^{2)}$(0.7 psi)=16.1 g/g (1 hr.); 18.0 g/g (3 hr.)

[1] Absorption under no load; and
[2] Absorption under load.

Absorption under load (AUL) is a measure of the ability of an SAP to absorb fluid under an applied pressure. The AUL was determined by the following method, as disclosed in U.S. Pat. No. 5,149,335, incorporated herein by reference.

An SAP (0.160 g±0.001 g) is carefully scattered onto a 140-micron, water-permeable mesh attached to the base of a hollow plexiglass cylinder with an internal diameter of 25 mm. The sample is covered with a 100 g cover plate and the cylinder assembly weighed. This gives an applied pressure of 20 g/cm² (0.28 psi). Alternatively, the sample can be covered with a 250 g cover plate to give an applied pressure of 51 g/cm² (0.7 psi). The screened base of the cylinder is placed in a 100 mm petri dish containing 25 milliliters of a test solution (usually 0.9% saline), and the polymer is allowed to absorb for 1 hour (or 3 hours). By reweighing the cylinder assembly, the AUL (at a given pressure) is calculated by dividing the weight of liquid absorbed by the dry weight of polymer before liquid contact. As discussed hereafter, the poly(vinylamine) particles also can be surface treated with a crosslinking agent, like ethyleneglycol diglycidyl ether, to give an absorbent having improved performance under external pressure.

In a preferred embodiment, a lightly crosslinked poly(vinylguanidine) is subjected to a process step wherein the surface of the poly(vinylguanidine) is further crosslinked. It has been found that surface crosslinking of a poly(vinylguanidine) enhances the ability of the polymer to absorb and retain aqueous media under load.

Surface crosslinking is achieved by spraying poly(vinylguanidine) particles with a water or alcohol solution of a surface crosslinking agent to wet predominantly only the outer surfaces of the poly(vinylguanidine) particles. Surface crosslinking and drying of the polymer then is performed, preferably by heating at least the wetted surfaces of the poly(vinylguanidine) particles.

Typically, the poly(vinylguanidine) particles are surface treated with an alcoholic solution of a surface crosslinking agent. The poly(VG) particles can be in the form of granules, a foam, beads, flakes, fibers, or powders, for example. The solution contains about 0.01% to about 4%, by weight, surface crosslinking agent, and preferably about 0.4% to about 2%, by weight, surface crosslinking agent in a suitable solvent. The solution can be applied as a fine spray onto the surface of freely tumbling poly(vinylguanidine) particles at a ratio of about 1:0.01 to about 1:0.5 parts by weight poly(vinylguanidine) to solution of surface crosslinking agent. The surface crosslinker is present in an amount of 0% to about 1%, by weight of the poly(vinylguanidine), and preferably 0 to about 0.5% by weight. To achieve the full advantage of the present invention, the surface crosslinker is present in an amount of about 0.005% to about 0.1% by weight.

The crosslinking reaction and drying of the surface-treated poly(vinylguanidine) particles are achieved by heating the surface-treated polymer at a suitable temperature, e.g., about 25° C. to about 150° C., and preferably about 105° C. to about 120° C. However, any other method of reacting the crosslinking agent to achieve surface crosslinking of the poly(vinylguanidine) particle, and any other method of drying the poly(vinylguanidine) particles, such as microwave energy, or the like, can be used.

Suitable surface crosslinking agents include the di- or polyfunctional molecules capable of reacting with amino groups and crosslinking poly(vinylguanidine). Preferably, the surface crosslinking agent is alcohol or water soluble and possesses sufficient reactivity with a poly(vinylguanidine) such that crosslinking occurs in a controlled fashion at a temperature of about 25° C. to about 150° C.

Nonlimiting examples of suitable surface crosslinking agents include:

(a) dihalides and disulfonate esters, for example, compounds of the formula

wherein p is a number from 2 to 12, and Z, independently, is halo (preferably bromo), tosylate, mesylate, or other alkyl or aryl sulfonate esters;

(b) monofunctional aldehydes, for example, formaldehyde and acetaldehyde;

(c) multifunctional aldehydes, for example, glutaraldehyde, trioxane, paraformaldehyde, terephthaldehyde, malonaldehyde, and glyoxal, and acetals and bisulfites thereof;

(d) halohydrins, like epichlorohydrin;

(e) multifunctional epoxy compounds, for example, ethylene glycol diglycidyl ether, bisphenol A diglycidyl ether, and bisphenol F diglycidyl ether, (f) melamine resins, like the CYMEL resins available from Cytec Industries, Wayne, N.J.; and (g) hydroxymethyl ureas, like N,N'-dihydroxymethyl-4,5-dihydroxyethylene urea.

A preferred surface crosslinking agent is ethylene glycol diglycidyl ether (EGDGE), which is a water-soluble diglycidyl ether which crosslinks poly(vinylguanidine) at a temperature of about 25° C. to about 150° C.

The following Example 4 illustrates surface treatment and crosslinking of a lightly crosslinked poly(vinylguanidine).

EXAMPLE 4

Surface Treatment of the Poly(VG) of Example 1

A surface-treating solution is prepared by admixing 0.15 grams EGDGE, 7.88 grams propylene glycol, and 1.97 grams deionized water until homogeneous. Ten grams of a lightly crosslinked poly(VG) are placed in a beaker fitted with a vertical shaft stirrer. The dry poly(VG) is stirred at a sufficient speed to fluidize the poly(VG) in the beaker, then 0.4 grams of the surface-treating solution is added to the fluidized poly(VG) dropwise via syringe. Then, stirring is stopped, and the beaker is placed in a 125° C. forced-air oven for one hour to yield a poly(VG) surface treated with 600 ppm of EGDGE. The surface-crosslinked poly (vinylguanidine) has an ability to absorb and retain greater than 15 times its weight, both AUNL and AUL, of 0.1 M hydrochloric acid.

Poly(vinylguanidine) does not function as an SAP in its neutral form because there is no ionic charge on the polymer. The driving force for water absorption and retention therefore is lacking. However, when converted to a salt, or used in conjunction with an acidic water-absorbing resin, like a polyacrylic acid, a poly(vinylguanidine) then behaves likes an SAP.

As previously discussed, sodium poly(acrylate) is considered the best SAP, and, therefore, is the most widely used SAP in commercial applications. Sodium poly(acrylate) has polyelectrolytic properties that are responsible for its superior performance in absorbent applications. These properties include a high charge density, and charge relatively close to the polymer backbone.

Poly(vinylguanidine) is a neutral polymer, and, accordingly, does not possess the polyelectrolytic properties necessary to provide an SAP. However, poly (vinylguanidine) salts have polyelectrolytic properties sufficient to provide an SAP. The poly(vinylguanidine) used to provide an SAP is a lightly crosslinked poly (vinylguanidine), and preferably is surface crosslinked, as set forth above.

Such lightly crosslinked, and optionally surface crosslinked, poly(vinylguanidine) polymers can be converted into salts by methods known in the art. For example, the preparation of poly(vinylamine HCl) by the addition of hydrochloric acid to a poly(vinylamine) is set forth in Pinschmidt, Jr. et al. U.S. Pat. No. 5,085,787, and in Gless, Jr. et al. U.S. Pat. No. 4,018,826. A poly(vinylguanidine) is a strongly basic resin, and is similarly converted to a salt.

A poly(vinylguanidine) salt useful as an SAP, however, is not limited to the hydrochloride salt. Poly(vinylguanidines) can be reacted with a variety of acids to provide a poly (vinylguanidine) salt useful as an SAP, but the preferred acids are mineral acids. To achieve the full advantage of the present invention, the poly(vinylguanidine) salt is a hydrochloride salt.

To demonstrate the ability of a poly(vinylguanidine) salt to act as an SAP, a lightly crosslinked poly(vinylguanidine) is converted to the hydrochloride salt by methods well known in the art. The poly(vinylguanidine) salt is tested for its ability to absorb and retain deionized water and electrolyte-containing aqueous media (i.e., 0.9% by weight aqueous sodium chloride).

In particular, lightly crosslinked poly(vinylguanidine) samples is converted to the hydrochloride salt using different amounts of 1N hydrochloric acid (HCl). The resulting gels of the poly(vinylguanidine) salts then are dried and evaluated for an ability to absorb a 0.9% by weight aqueous NaCl solution. A lightly crosslinked poly(vinylguanidine) neutralized 70 mole % with hydrochloric acid absorbed 31.2 g of the saline solution per gram of resin, under no load, after 3 hours; 21.0 g/g under a 0.28 psi load after 3 hours; and 16.1 g/g under a 0.7 psi load after 3 hours.

These absorbency results show that absorbency increases dramatically, both under load and under no load, when the poly(vinylguanidine) is converted to a hydrochloride salt, especially in the range of about 15 to about 85 mole % conversion to the salt. In accordance with an important feature of the present invention, a poly(vinylguanidine) exhibits the properties of an SAP when converted to a salt in an amount of about 10 to about 100, and preferably about 20 to about 90, mole percent. To achieve the full advantage of the present invention, the poly(vinylguanidine) is converted to a salt in an amount of about 15 to about 85 mole %, based on the weight of N-vinylamide monomer used to prepare the poly(vinylguanidine).

As illustrated above, poly(vinylguanidine), in its free base form, does not function as an SAP for neutral-to-basic aqueous media. Similarly, polyacrylic acid, in its free acid form, does not function as an SAP for neutral-to-acidic aqueous media. In each case, the polymer has a low charge density, and, accordingly, a major driving force for absorption and retention, i.e., electrostatic repulsion, is missing. In contrast, partially neutralized polyacrylic acid has a sufficient charge density, and is currently used as an SAP by itself. Similarly, as disclosed above, poly(vinylguanidine) salts have a high charge density and are excellent SAPs.

However, a poly(vinylguanidine), in its free base form, can act as an absorbent for acidic aqueous media, i.e., media having a pH less than 7. The acidic media protonates the amino groups of the poly(vinylguanidine), thereby providing sufficient charge density for the protonated poly (vinylguanidine) to perform as an SAP. Accordingly, poly (vinylguanidine), by itself, can be used to absorb acidic aqueous media, for example, to absorb an acid spill.

It also has been found that poly(vinylguanidine) polymers, in their free base form, are useful components in superabsorbent materials further containing an acidic water-absorbing resin. For example, a superabsorbent material of the present invention is an admixture of a poly (vinylguanidine) and an acidic water-absorbing resin, like polyacrylic acid. The present superabsorbent materials are particularly useful with respect to absorbing and retaining aqueous media containing electrolytes.

Currently, superabsorbent materials containing two absorbing components, i.e., bi-component SAP materials, are being investigated as an improved class of SAPs. Typically, one component is a water-absorbing resin, and the second component acts in an ion exchange capacity to remove electrolytes from an aqueous media.

In contrast, the present invention is directed to a bi-component SAP material comprising two uncharged, slightly crosslinked polymers, each of which is capable of swelling and absorbing aqueous media. When contacted with water or saline, the two uncharged polymers neutralize each other to form a superabsorbent material. Neither polymer in its uncharged form behaves as an SAP by itself when contacted with water. The present bi-component superabsorbent material, therefore, contains two resins, one acidic and one basic, which are capable of acting as an absorbent material in their polyelectrolyte form. While polyacrylic acid is an excellent choice for the acidic resin, until the present invention, there has not been an adequate basic resin.

Therefore, in accordance with an important feature of the present invention, poly(vinylguanidine) is used as the basic resin for a bi-component SAP material. The poly (vinylguanidine) is lightly crosslinked, and the poly (vinylguanidine) particles, or granules, preferably are surface crosslinked to improve absorbency characteristics. Crosslinking and surface crosslinking can be performed as set forth above. The poly(vinylguanidine) and acid resin combination behaves like an SAP in the presence of water, and especially brackish water.

The poly(vinylguanidine) is a basic resin that is admixed with an acidic resin. The acidic resin can be any resin that acts as an SAP in its neutralized form. The acidic resin typically contains a plurality of carboxylic acid, sulfonic acid, sulfuric acid, phosphonic acid, or phosphoric acid moieties, or a mixture thereof.

Examples of acidic resins include, but are not limited to, polyacrylic acid, hydrolyzed starch-acrylonitrile graft copolymers, starch-acrylic acid graft copolymers, saponified vinyl acetate-acrylic ester copolymers, hydrolyzed acrylonitrile copolymers, hydrolyzed acrylamide copolymers, ethylene-maleic anhydride copolymers, isobutylene-maleic anhydride copolymers, poly(vinylsulfonic acid), poly(vinylsulfuric acid), poly(vinylphosphonic acid), poly(vinylphosphoric acid), sulfonated polystyrene, and mixtures thereof. The preferred acidic resins are the polyacrylic acids.

The poly(vinylguanidine) is present in its uncharged, i.e., free base, form, and the acidic resin is present in its free acid form. It is envisioned that a low percentage, i.e., 25% or less, of the amine and acid functionalities can be in their charged form, due to processing, for example. The low percentage of charged functionalities does not adversely affect performance of the superabsorbent material, but the amount of charged functionalities should be minimized.

The poly(vinylguanidine) and acidic resin are admixed in a weight ratio of about 5:95 to about 95:5, and preferably about 10:90 to about 90:10. To achieve the full advantage of the present invention, the resins are admixed in a weight ratio of about 30:70 to about 70:30. A present bi-component SAP material is prepared by simply admixing particles of the poly(vinylguanidine) and acidic resin to provide a uniform particulate material.

To illustrate a present bi-component SAP material, the following examples can be prepared and tested:

EXAMPLE 5

Lightly crosslinked, powdered poly(vinylguanidine) (containing 12% by weight vinylguanidine units and having a particle size 210–710 μm) is admixed with lightly crosslinked polyacrylic acid (particle size 210–710 μm, 0% neutralized) in a weight ratio of 50% poly(VG) to 50% polyacrylic acid. The absorbency characteristics of the resulting bi-component SAP are improved with respect to absorbing and retaining a 0.9% by weight aqueous NaCl solution. The poly-(VG)/polyacrylic acid blend has improved absorption properties compared to poly(VG) alone.

The bi-component SAP materials are especially useful in articles designed to absorb and retain liquids, especially electrolyte-containing liquids. Such articles include, for example, diapers and catamenial devices.

Many modifications and variations of the invention as hereinbefore set forth can be made without departing from the spirit and scope thereof and, therefore, only such limitations should be imposed as are indicated by the appended claims.

What is claimed is:

1. A solid superabsorbent material comprising a mixture of
   (a) discrete particles of a lightly crosslinked poly(vinylguanidine) having the structure

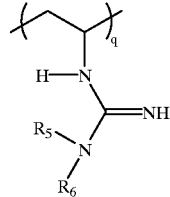

wherein q is a number from 10 to about 10,000, and $R_5$ and $R_6$, independently, are selected from the group consisting of hydrogen, $C_1$–$C_4$ alkyl, $C_3$–$C_6$ cycloalkyl, benzyl, phenyl, alkyl-substituted phenyl, and naphthyl, and is lightly crosslinked with a crosslinking agent selected from the group consisting of divinylbenzene; divinyl ether;

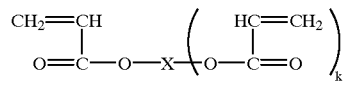

wherein x is ethylene, propylene, trimethylene, hexamethylene, 2-hydroxypropylene, —$(CH_2CH_2O)_n$ $CH_2CH_2$—;

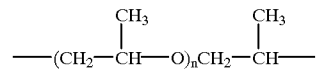

n and m are each an integer 5 to 40, and k is 1 or 2;

wherein l is 2 or 3; a monofunctional aldehyde; a multifunctional aldehyde; a multifunctional acrylate; a halohydrin; a dihalide; a disulfonate ester; a multifunctional epoxy; a melamine resin; a hydroxymethyl urea; and mixtures thereof, and (b) discrete particles of an acidic water-absorbing resin.

2. The superabsorbent material of claim 1 wherein the acidic resin is selected from the group consisting of polyacrylic acid, a hydrolyzed starch-acrylonitrile graft copolymer, a starch-acrylic acid graft copolymer, a saponified vinyl acetate-acrylic ester copolymer, a hydrolyzed acrylonitrile copolymer, a hydrolyzed acrylamide copolymer, an ethylene-maleic anhydride copolymer, an isobutylene-maleic anhydride copolymer, a poly(vinylsulfonic acid), a poly(vinylsulfuric acid), a poly(vinylphosphonic acid), a poly(vinylphosphoric acid), a sulfonated polystyrene, and mixtures thereof.

3. The superabsorbent material of claim 1 wherein the poly(vinylguanidine) and the acidic resin are present in a weight ratio of about 5:95 to about 95:5.5.

4. An article comprising the superabsorbent material of claim 1.

5. The superabsorbent material of claim 1 wherein $R_5$ and $R_6$ are hydrogen.

6. The superabsorbent material of claim 1 wherein $R_5$ is hydrogen and $R_6$ is selected from the group consisting of methyl, phenyl, and benzyl.

7. The superabsorbent material of claim 1 wherein the poly(vinylguanidine) comprises about 10% to 100% vinylguanidine units.

* * * * *